United States Patent [19]

Olah

[11] Patent Number: 4,467,130

[45] Date of Patent: * Aug. 21, 1984

[54] CONDENSATION OF NATURAL GAS OR METHANE INTO GASOLINE-RANGE HYDROCARBONS

[76] Inventor: George A. Olah, 2252 Gloaming Way, Beverly Hills, Calif. 90210

[*] Notice: The portion of the term of this patent subsequent to Aug. 14, 2001 has been disclaimed.

[21] Appl. No.: 504,738

[22] Filed: Jun. 16, 1983

Related U.S. Application Data

[62] Division of Ser. No. 298,486, Sep. 1, 1981, Pat. No. 4,433,192.

[51] Int. Cl.$^3$ .............................................. C07C 3/44
[52] U.S. Cl. ................................... 585/709; 585/723; 585/732; 585/943; 585/400; 585/500; 585/700; 502/224
[58] Field of Search ............... 585/415, 943, 945, 709, 585/711, 717, 721, 723, 724, 730, 732; 502/224

[56] References Cited

U.S. PATENT DOCUMENTS

| | | | |
|---|---|---|---|
| 3,636,129 | 1/1972 | Parker et al. | 585/709 |
| 3,678,120 | 7/1972 | Bloch | 585/730 |
| 3,809,728 | 5/1974 | Kemp et al. | 585/724 |
| 3,852,371 | 12/1974 | Kemp | 585/724 |
| 3,960,764 | 6/1976 | Bernard et al. | 585/730 |
| 3,979,476 | 9/1976 | Kemp | 585/724 |
| 4,025,577 | 5/1977 | Siskin et al. | 585/724 |
| 4,035,286 | 7/1977 | McCauley et al. | 585/717 |
| 4,044,069 | 8/1977 | Bernard et al. | 585/730 |
| 4,065,381 | 12/1977 | Say et al. | 585/730 |
| 4,162,233 | 7/1979 | Kremer | 585/942 |

FOREIGN PATENT DOCUMENTS 2372133 11/1976 France .............................. 585/724

*Primary Examiner*—Delbert E. Gantz
*Assistant Examiner*—Asokkumar Pal
*Attorney, Agent, or Firm*—Pennie & Edmonds

[57] ABSTRACT

This invention relates to a new process for the direct conversion of natural gas or methane into gasoline-range hydrocarbons (i.e., synthetic transportation fuels or lower olefins) via catalytic condensation using superacid catalysts.

4 Claims, No Drawings

CONDENSATION OF NATURAL GAS OR METHANE INTO GASOLINE-RANGE HYDROCARBONS

This is a division of application Ser. No. 298,486 filed Sept. 1, 1981, now U.S. Pat. No. 4,433,192.

TECHNICAL FIELD

This invention relates to the direct conversion of natural gas or methane into gasoline-range hydrocarbons (i.e., synthetic transportation fuels or lower olefins) via catalytic condensation using superacid catalysts.

BACKGROUND ART

The present state of art for production of synthetic fuels from either coal or natural gas (the two major possible raw materials) involves initial production of synthesis gas which is then either converted directly to hydrocarbons (Fischer-Tropsch) or converted first to methyl alcohol, which subsequently is converted into hydrocarbons (Mobil process):

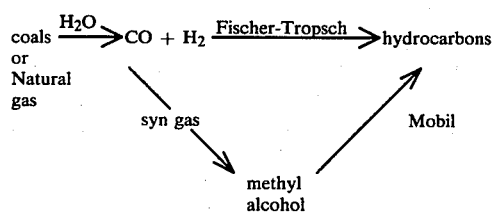

The Fischer-Tropsch process, although proven commercially, is not the most economically desirable process for the future due to its two very energetic steps and unsuitable product composition. The Mobil process is capable of producing gasoline-range hydrocarbons and aromatics relatively free of heavies, but suffers from the disadvantageous economics of first producing synthesis gas, which is then converted into methyl alcohol, which in turn is converted into hydrocarbons.

My discovery follows an independent and new route by utilizing methane (or natural gas) as the basic raw material. Methane as natural gas or even biological "deep methane" is expected to be available well into the 2000's, and, if not utilized exclusively as an energy source but rather for transportation fuels and as a chemical raw material source, could last much longer. Furthermore, coal can be readily converted into methane by methanation or by in-situ gasification, thus avoiding difficulties in mining and transporting coal. Further, alternate sources of methane, such as the biological conversion of biomass (sewage recycling, utilization of plant life on land and sea [algae or kelp farming of the sea] with subsequent off shore conversion allowing the piping of methane to land), are becoming available. If in the future cheaper atomic or fusion energy becomes available, during off-peak periods, these plants could become producers of aluminum carbide which, upon hydrolysis, gives methane (with ethane and ethylene as by-products.) The conversion of methane to higher hydrocarbons thus represents a viable new alternative to synthetic hydrocarbon processes.

The oligocondensation of methane was discovered by Olah et al., *Journal of the American Chemical Society*, 90, 2726 (1968), using exceedingly strong acid systems, the so-called "superacids" comprising a mixture of fluorosulfuric acid and antimony pentafluoride ("magic acid"), a mixture of hydrogen fluoride and antimony pentafluoride, or related superacids. Superacids have a Hammett acidity function $H_o$ less than $-11.9H_o$, the value for 100 percent sulfuric acid. However, yields were extremely low and the superacid was reductively depleted, rendering the process impractical on a commercial scale.

Alkane-alkene condensations (alkylations) such as that of isobutane with isobutylene to produce $C_8$ alkylate is well known in the petrochemical industry. Olah reported first the alkylation of alkanes with alkyl cations, generated in superacidic media [J.Am.Chem.Soc., 96, 4939–4952 (1973)].

The condensation (polymerization) of methane and olefins represents a special problem and for a long time, methane was considered to be inert to usual acid catalyzed electrophilic reactions. The work of Olah on the superacid catalyzed reactivity of methanes opened up the possibility for such reactions. D. T. Roberts, Jr. and L. E. Calihan [J.Macronol.Sci-Chem., A7 (8) pp. 1641–1646 (1973)] reported that mixtures of methane and olefins (ethylene, propylene, etc.) polymerized in an autoclave at room temperature over a liquid magic acid ($HSO_3F/SbF_5$) catalyst to give oily oligomers with molecular weight of 100 to 700. Conversions were low (in the case of methane and ethylene, 5%) and under the used liquid phase conditions with long contact times (generally 24 hours) the olefin itself tended to polymerize on its own. Subsequently using another liquid superacid catalyst, hydrogen fluoride-tantalum pentafluoride, Siskin carried out the alkylation of methane with ethylene in a pressurized flow system [J.Am.Chem. Soc., 98, 5413 (1976)]. No yields or conversions were given and again the liquid phase reaction conditions were considered to substantially limit practical application of the reaction.

DESCRIPTION OF THE INVENTION

In sharp contrast to previous practice, there now exists a practical way to condense methane with lower olefins, readily available via dehydrogenation of natural gas, and/or acetylene utilizing a solid or supported superacid catalyst under heterogeneous gas-phase conditions with short contact times, thus minimizing or eliminating the olefin polymerization which makes the liquid phase system unsuitable for practical processes.

The condensation of methane into higher hydrocarbons must overcome the unfavorable endothermic thermodynamics of such individual steps as noted below:

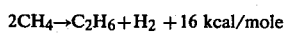

$$2CH_4 \rightarrow C_2H_6 + H_2 + 16 \text{ kcal/mole}$$

In order to overcome this difficulty, it is necessary to oxidatively remove hydrogen. The removal of hydrogen has now been discovered to be possible in two ways.

The first method involves the dehydrogenation of natural gas to a mixture of methane and lower olefins (ethylene, with some propylene and butenes) or, alternatively, its thermal treatment to form acetylene, (as well as ethylene) and condensing these mixtures in the presence of a superacidic catalyst to hydrocarbons in the gasoline-range:

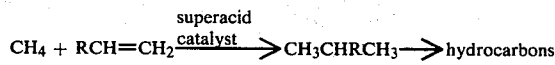

R = H, CH$_3$, C$_2$H$_5$ or,

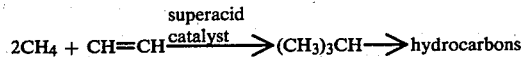

The useful catalysts can be selected from higher valency Lewis acid fluorides of metals of Groups IV, V and VI of the Periodic Table such as tantalum pentafluoride, niobium pentafluoride, antimony pentafluoride and the like, supported on a suitable carrier, such as fluoridated alumina, alumina, alumina-silica, silica or the like.

Useful catalysts can also be selected from superacidic conjugated acids composed of a strong Bronsted acid such as hydrogen fluoride, fluorosulfuric acid, perfluoroalkane-sulfonic acids of 1 to 18 carbon atom length, supported on a suitable solid carrier, or polymeric perfluorinated acids such as Nafion-H or copolymers of perfluorovinyl perfluorinated polymeric resin-sulfonic acids and the like, in conjunction with a suitable Lewis acid fluoride, such as those of the metals of Groups IV, V and VI of the Periodic Table.

The solid or supported solid catalysts are used at temperatures between 50° and 250° C. and pressures of 1 to 150 or more atmospheres. The feed mixtures generally contain a substantial excess of methane, in mole ratios of 6 to 12:1 to olefins and/or acetylene, readily obtainable from pretreatment of natural gas by catalytic dehydrogenation or thermal reaction.

These condensations generally produce isoalkane mixtures, as well as cycloalkanes and aromatics of less than 12 carbons but no olefins.

The second method involves the oxidative condensation of methane, in which an oxidizing agent, such as air, oxygen, oxygen-ozone mixture, sulfur, selenium, sulfur trioxide, nitrogen oxides, halogens (fluorine, chlorine, bromine, iodine) is utilized to remove hydrogen as noted below.

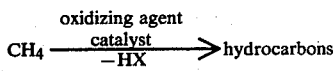

The condensation reaction can be achieved in a single step or can be carried out in two steps.

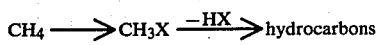

X = OH, SH, halogen

The conventional oxidation of methane, involving radical processes can not be carried out selectively to methyl alcohol. It is, however, possible to oxidize methane to a mixture of methyl alcohol and formaldehyde with, for example, short contact time at temperatures around 600° C. and 60 atm. It is also part of my discovery that methyl alcohol-formaldehyde mixtures, i.e., methylal (dimethoxymethane), can be directly condensed into higher hydrocarbons over bifunctional supported acid-base catalysts, such as 10% WO$_3$ on alumina. The methyl alcohol (through dimethyl ether) or methyl alcohol and formaldehyde (through methylal) condensations over bifunctional supported acid-base catalysts yield similar product mixtures as disclosed in my co-pending application Ser. No. 298,390

I have discovered that when oxidizing methane with the aforementioned oxidizing agent such as O$_2$, or O$_2$–O$_3$ mixtures in the presence of bifunctional supported acidic-basic catalysts, such as those described in my co-pending application Ser. No. 290,292 and based on bifunctional acidic oxides or halides, such as those of tantalum, niobium, zirconium, tungsten, titanium, chromium and the like, on carriers such as alumina, silica, silica-alumina, zirconia, arconia and the like, results in selective electrophilic oxygenation by surface bound species such as +O$_3$H, +O$_2$H. As the oxidation reaction is carried out in the presence of condensing catalysts described in my co-pending application Ser. No. 298,486, condensation to higher hydrocarbons is directly achieved.

The oxidative condensation of methane can also be realized with sulfur or selenium as oxidizing agents. The thermal or catalytic reaction of sulfur with methane at relatively low (approximately 450° C.) temperatures gives methyl mercaptan, dimethyl sulfide, and carbon disulfide. The latter can be converted to methyl mercaptan with hydrogen in the presence of acid catalysts. Methyl mercaptan and/or dimethyl sulfide can be subsequently or simultaneously again condensed to hydrocarbons.

The oxidative condensation of methane with sulfur gives H$_2$S as by-product. It can be readily oxidized to recover sulfur or, alternatively, it was discovered that by combining a CO shift reaction over a supported molybdenum sulfide catalyst with catalytic or thermal decarbonylation of COS, it is possible to obtain hydrogen and regenerate sulfur, thus allowing the following condensation:

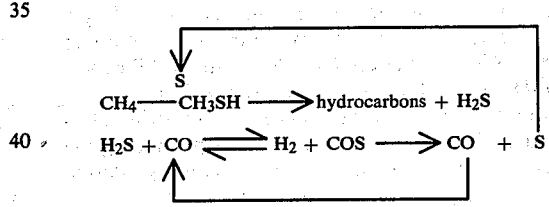

to proceed to hydrocarbons and hydrogen. This approach allows a methane condensation with the recovery of hydrogen, or is also applicable to hydrogen production from refinery gases, sour gas wells or coal desulfurization.

The oxidative condensation of methane can also be carried out with halogens as the oxidizing agents. Methane can be chlorinatively (brominatively, iodinatively) condensed under the reaction conditions. Initially, methyl chloride, bromide, or iodide are formed (or methyl fluoride if the halogenation is carried out in the presence of HF) which are subsequently readily condensed into higher hydrocarbons. HCl, HBr or HI are recycled via oxyhalogenation, whereas HF is reusable as such. The condensation reaction is preferably carried out at a temperature of 50° to 250° C. and at a pressure of 1 to 150 atmospheres.

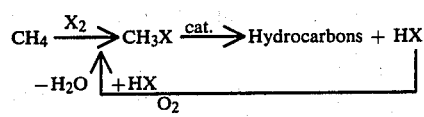

X = Cl, Br, I or,

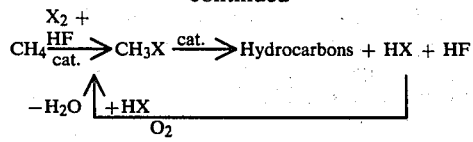

It is further part of my discovery that by converting methane selectively through its suitable monosubstituted derivatives using superacid catalyzed ionic reactions, with high selectivity as detailed in my co-pending application Ser. No. 290,260, a two-step process can also be efficiently operated with subsequent or concurrent condensation giving higher hydrocarbons.

Illustrative of the invention are the following examples, set forth for the purpose of illustration only and not to be construed as limiting the scope of the invention in any matter. In the related Tables where product compositions are given, they have been normalized, even if not stated, to provide a total of 100% conversion, excluding unreacted methane which can be recycled.

EXAMPLE 1

Natural gas containing about 82% methane and 18% ethane, with some propane and butane, is subjected to conventional catalytic dehydrogenation (cracking), yielding, in addition to unreacted methane, an ethylene-propylene containing feed which after drying can be utilized directly in the condensation reaction. The obtained methane-ethylene feed (in about 90:10 ratio) containing some ethane, propylene, butylenes, which do not need to be separated, is reacted over a tantalum pentafluoride catalyst supported on fluoridated alumina (10% per weight), at a temperature of 70° C. in a continuous flow reactor. A 38% conversion per pass (based on reacted ethylene) is obtained with the following composition:

| Product composition | (%)[a] |
| --- | --- |
| $C_2H_6$ | 10 |
| $C_3H_8$ | 12 |
| i-$C_4H_{10}$ | 48 |
| n-$C_4H_{10}$ | 6 |
| i-$C_5H_{12}$ | 15 |
| n-$C_5H_{12}$ | 5 |
| < $C_5$ | 4 |

[a]methane excluded and normalized to 100%

EXAMPLE 2

A feed mixture consisting of about 88% methane and 10% acetylene was treated through under the conditions of example 1 over the supported tantalum pentafluoride at 70° C. in the continuous flow reactor. A 78% conversion per pass (based on feed acetylene) was obtained with the following product distribution:

| Product distribution | (%)[a] |
| --- | --- |
| $C_2H_6$ | 3 |
| $C_3H_8$ | 6 |
| i-$C_4H_{10}$ | 81 |
| n-$C_4H_{10}$ | <1 |
| i-$C_5H_{12}$ | 5 |
| n-$C_5H_{12}$ | <1 |
| > $C_5$ | 3 |

EXAMPLE 3

Under the conditions of example 2, a feed mixture consisting of about 80% methane, 10% ethylene and 10% acetylene was passed through the supported tantalum pentafluoride catalyst at 70° C. A 68% conversion per pass was obtained with the following product composition:

| % Product composition[a] | |
| --- | --- |
| ethane | 22 |
| propane | 1 |
| butanes | 16 |
| pentanes | 39 |
| hexanes | 22 |

EXAMPLE 4

A 9:1 natural gas (consisting about 90% methane and 10% ethane)-oxygen mixture was reacted at a pressure of 80 atm at 380° C. over a 10% tungsten oxide on alumina catalyst. The conversion obtained (based on oxygen available) was 31% of theoretical. The hydrocarbon product contained 28.9% ethylene and 34.6% propylene, with the balance being oxygenated products and small amounts of butylenes and trace amounts and ethane, propane and butanes.

EXAMPLE 5

Methane was reacted in the presence of selenium in the ratio of 5:1, in the presence of the tantalum pentafluoride catalyst at 200° C. in a stainless steel pressure autoclave for six hours. A 16% conversion to condensed saturated hydrocarbons was obtained with the following product composition:

| % Product composition[a] | |
| --- | --- |
| ethane | 24 |
| propane | 2 |
| isobutane | 37 |
| pentanes | 18 |
| hexanes | 19 |

EXAMPLE 6

A 2:1 methane-chlorine mixture was reacted over a perfluorinated resinsulfonic acid (Nafion-H) catalyst complexed with 20% tantalum pentafluoride at 185° C. in the previously utilized continuous flow reactor. 40% per pass conversion gave the following product composition:

| % Product composition[a] | |
| --- | --- |
| methyl chloride | 2 |
| methylene chloride | 7 |
| ethane | 3 |
| ethyl chloride | 40 |
| isobutane | 48 |

I claim:

1. A process for the heterogeneous gas-phase condensation of natural gas or methane into gasoline-range hydrocarbons comprising the steps of:
   (a) thermally pretreating the natural gas or methane to form an acetylene-containing mixture;

(b) condensing the resulting methane-acetylene-containing mixture in the presence of a superacid catalyst having a Hammett acidity function $H_o$ less than $-11.9$ to hydrocarbon mixtures in the gasoline range.

2. The process of claim 1 carried out utilizing solid superacid catalysts of strong Lewis acid fluorides of metals of Groups IV, V or VI of the Periodic Table, deposited on a chalconide carrier including alumina, silica, alumina-silica, or floridated alumina.

3. The process of claim 1 carried out utilizing a conjugate solid superacid catalyst composed of a strong Bronsted acid component selected from fluorosulfuric acid, perfluoroalkanesulfonic acids of 1 to 18 carbon atoms deposited on a suitable carrier, perfluorinated polymeric resinsulfonic acids or co-polymers of perfluorovinylsulfonic acid and tetrafluoroethylene or trifluorochloroethylene complexed with a Lewis acid fluoride of a metal of Groups IV, V or VI of the Periodic Table.

4. The process of claim 1 carried out at a temperature between 50° to 250° C. and a pressure of 1 to 150 atmospheres.

* * * * *